United States Patent [19]
Kurashina et al.

[11] Patent Number: 4,940,715
[45] Date of Patent: Jul. 10, 1990

[54] 5H-PYRAZOLO[4,3-A] QUINOLIZIN-5-ONE COMPOUNDS EXHIBITING THERAPEUTIC ACTIVITIES

[75] Inventors: Yoshikazu Kurashina; Hiroshi Miyata; Den-ichi Momose, all of Matsumoto, Japan

[73] Assignee: Kissei Pharmaceutical Co., Ltd., Japan

[21] Appl. No.: 349,778

[22] Filed: May 10, 1989

[30] Foreign Application Priority Data

May 17, 1988 [JP] Japan ................................. 62-120297
May 17, 1988 [JP] Japan ................................. 63-120298

[51] Int. Cl.$^5$ ............................................. C07D 471/06
[52] U.S. Cl. ........................................ 514/293; 546/82
[58] Field of Search .......................... 546/82; 514/293

[56] References Cited

U.S. PATENT DOCUMENTS

| 3,968,119 | 7/1976 | Harnisch | 546/82 X |
| 4,223,032 | 9/1980 | Buckle et al. | 546/82 X |
| 4,602,014 | 7/1986 | Yokoyama | 546/82 X |

Primary Examiner—Mary C. Lee
Assistant Examiner—Catherine S. Kilby Scalzo
Attorney, Agent, or Firm—DePaoli & O'Brien

[57] ABSTRACT

This invention provides novel 5H-pyrazolo[4,3-a]-quinolizin-5-one compounds which exhibit a selective inhibitory activity against IgE-antibody formation, and have utility for treatment of allergic diseases associated with IgE formation in mammals, such as allergic bronchial asthma, allergic rhinitis, atopic dermaties, hypersensitiveness, and the like.

7 Claims, No Drawings

5H-PYRAZOLO[4,3-A] QUINOLIZIN-5-ONE COMPOUNDS EXHIBITING THERAPEUTIC ACTIVITIES

FIELD OF THE INVENTION

This invention relates to novel pyrazoloquinolizinone derivatives having utility as therapeutic agents. More particularly, this invention provides 5H-pyrazolo[4,3-a]quinolizin-5-one compounds which exhibit anti-allergic activities and which have properties suitable for application as drugs for allergic diseases such as allergic bronchial asthma, allergic rhinitis, atopic dermatitis, hypersensitiveness and the like.

BACKGROUND OF THE INVENTION

Many kinds of anti-allergic drugs have been utilized for treatment of allergic diseases.

Among these drugs, the release-inhibitors of allergic chemical mediators have been widely used as the drugs for causal treatment.

More recently, the inhibitors of immunoglobulin E (hereinafter referred to as IgE) antibody formation have been receiving attention as prospective drugs for causal treatment, since IgE has been confirmed to be primarily responsible for pathogenesis of type I allergic diseases.

Several classes of immunoglobulin(s) [hereinafter referred to as Ig(s)] are well known as antibodies concerned with immune response. Most of Igs, especially immunoglobulin G (hereinafter referred to as IgG) which is one class of Igs, play an important role in self-defense mechanisms in mammals against foreign substances such as viruses, bacteria, tumors and the like. However, IgE has been confirmed to be primarily responsible for diseases such as allergic bronchial asthma, allergic rhinitis, atopic dermatitis, hypersensitiveness, and the like.

Therefore, selective inhibition of IgE formation might be an effective pharmacological approach for the treatment of allergy in the human. And attempts have been widely made to develop the selective inhibitors of IgE formation. The prospective inhibitors preferably would not inhibit excessively any class of Igs except IgE for reasons mentioned above.

Up to the present time, various compounds have been reported to inhibit IgE formation in literature such as Japanese Patent Application (OPI) Nos. 130516/79 and 76/87 (the term "OPI" used herein refers to an unexamined Japanese patent publication); U.S. Pat. Nos. 4,395,405 and 4,691,018; British Patent Application No. 2,020,665 (A) and J. Med. Chem. Vol. 25, No. 12, pages 1495–1499, 1982.

However, these compounds reported above as an inhibitor of IgE formation have been confirmed to exhibit less selectivity and have not been applicable yet.

CROSS-REFERENCE TO RELATED APPLICATIONS

The subject matter of the present invention is related to that disclosed in U.S. patent application Ser. No. 147,549, filed January 25, 1988; U.S. patent application Ser. No. 244,269, filed September 15, 1988; and U.S. patent application Ser. No. 269,301, filed November 10, 1988.

SUMMARY OF THE INVENTION

Accordingly, an object of this invention is to provide novel 5H-pyrazolo[4,3-a]quinolizin-5-one compounds which exhibit selective inhibitory activities against IgE formation when administered to human or to other mammals.

Another object of this invention is to provide 5H-pyrazolo[4,3-a]quinolizin-5-one compounds which are useful for the treatment of allergic diseases such as allergic bronchial asthma, allergic rhinitis, atopic dermatitis, hypersensitiveness, and the like.

Other objects, features and advantages of this invention will be apparent from the following description of the invention.

This invention provides novel 5H-pyrazolo[4,3-a]quinolizin-5-one compounds represented by the formula:

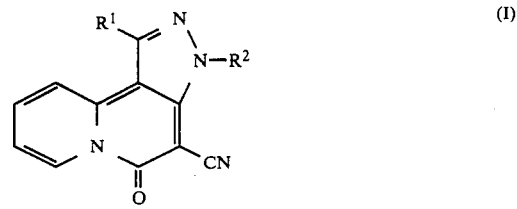

where $R^1$ is an alkyl group having 1 to 10 carbon atoms, a substituted or unsubstituted phenyl group having 6 to 10 carbon atoms, or a substituted or unsubstituted phenylalkyl group having 7 to 10 carbon atoms; $R^2$ is a hydrogen atom, an alkyl group having 1 to 3 carbon atoms, a substituted or unsubstituted phenyl group having 6 to 10 carbon atoms, an aliphatic acyl group having 2 to 6 carbon atoms, or a substituted or unsubstituted benzoyl group having 7 to 10 carbon atoms.

In another embodiment this invention provides a 5H-pyrazolo[4,3-a]quinolizin-5-one compound corresponding to the formula:

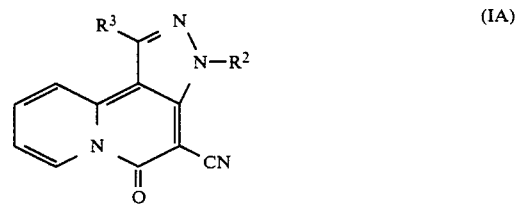

where $R^2$ is as previously defined; $R^3$ is an alkyl group having 1 to 4 carbon atoms.

DETAILED DESCRIPTION OF THE INVENTION

The 5H-pyrazolo[4,3-a]quinolizin-5-one derivatives of this invention selectively inhibit the formation of IgE.

Pharmacological test data indicated that the 5H-pyrazolo[4,3-a]quinolizin-5-one derivatives of formula (I) of this invention exhibit selective inhibitory activities against IgE formation and have a potential utility as drugs for allergic diseases such as allergic bronchial asthma, allergic rhinitis, atopic dermatitis, hypersensitiveness, and the like.

The 5H-pyrazolo[4,3-a]quinolizin-5-one compounds of formula (I) of this invention can be prepared as follows.

Of the 5H-pyrazolo[4,3-a]quinolizin-5-one compounds of formula (I), the compounds corresponding to the formula:

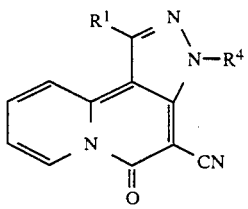
(Ib)

where $R^1$ is as previously defined, and $R^4$ is a hydrogen atom, an alkyl group having 1 to 3 carbon atoms or a substituted or unsubstituted phenyl group having 6 to 10 carbon atoms, can be prepared by the reaction of the 4H-quinolizin-4-one compounds corresponding to the formula:

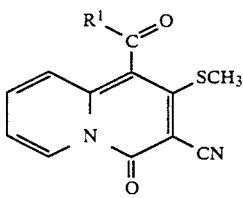
(II)

where $R^1$ is as previously defined, with hydrazine compounds corresponding to the formula:

 (III)

where $R^4$ is as previously defined.

Of the 5H-pyrazolo[4,3-a]quinolizin-5-one compounds of formula (I), the compounds corresponding to the formula:

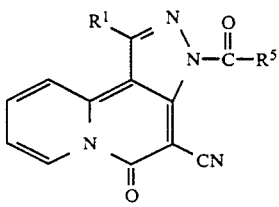
(Ic)

where $R^1$ is as previously defined; and $R^5$ is an and group having 1 to 5 carbon atoms or a substituted or unsubstituted phenyl group having 6 to 10 carbon atoms, can be prepared by the reaction of 5H-pyrazolo[4,3-a]quinolizin-5-one compounds corresponding to the formula:

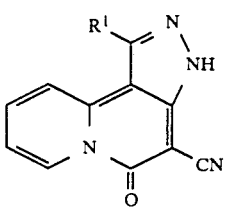
(Id)

where $R^1$ is as previously defined, with acid anhydrides corresponding to the formula:

 (IV)

where $R^5$ is as previously defined.

The 4H-quinolizin-4-one compounds of formula (II) for use as starting materials can be prepared according to the method described by Kobayashi et al. in Yakugaku Zasshi Vol. 89, No. 2, pp 203–208, 1969.

Thus, they can be prepared by the reaction of compounds corresponding to the formula:

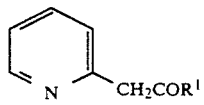
(V)

where $R^1$ is as previously defined, with a compound corresponding to the formula:

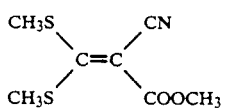
(VI)

The compounds of formula (V) can be prepared according to the manner described in Helvetica Chimica Acta, Vol. 45, pp 729–737, 1962.

And the compounds of formula (VI) can be prepared in accordance with a procedure described in Chemische Berichte, Vol. 95, pp 2861–2870, 1962.

Compounds of formulae (III) and (IV) for use as other starting materials are commercially available.

The reaction of a compound of formula (II) with a compound of formula (III) can be conducted in accordance with the following preferred method.

To a solution of a compound of formula (II) in an suitable organic solvent such as dimethyl sulfoxide is added a hydrazine compound of formula (III) in an excess quantities, and the mixture is stirred at room temperature or under mild warming for several hours, and then a volume of cold water is added to the reaction mixture. The precipitated crystals are collected by filtration and successively washed with water and an organic solvent, and dried to obtain a compound of formula (Ib).

And the reaction of a compound of formula (Id) with a compound of formula (IV) can be conducted as follows.

A mixture of a compound of formula (Id) and a compound of formula (IV) is heated for 2–20 hours, and the reaction mixture is evaporated under reduced pressure to remove an excess of the compound of formula (IV). The residual crystals are successively washed with water and an organic solvent and dried to obtain a compound of formula (Ic).

The 5H-pyrazolo[4,3-a]quinolizin-5-one compounds of formula (I) of the present invention exhibit selective inhibitory activities on IgE formation. The inhibitory activities of the pyrazoloquinolizinone compounds of formula (I) are confirmed by the determination of Igs produced in cultures of spleen cells from BALB/c mice which exhibit an adoptive secondary immune response against dinitrophenylated proteins of ascaris (DNP-As) according to a procedure described in Cellular Immunology, Vol. 58, pp 188–201, 1981. The antiallergic activities of the 5H-pyrazolo[4,3-a]quinolizin-5-one compounds of formula (I) are also confirmed by inhibition of the rat homologous passive cutaneous anaphylaxis (hereinafter referred to as PCA) reaction.

The results obtained by these tests demonstrate that the compounds of formula (I) of this invention inhibit IgE formation and minimally affect the production of Igs other than IgE, and exhibit the antiallergic activities.

From the results obtained by these pharmacological tests, it can be expected that the compounds of formula (I) of this invention have properties suitable for application as a therapeutic agent for the treatment of allergic diseases associated with IgE in mammals.

An acute toxicological test in mice shows that the compounds of formula (I) of this invention have very low acute toxicity.

Of the 5H-pyrazolo[4,3-a]quinolizin-5-one compounds of formula (I), the compounds corresponding to the formula:

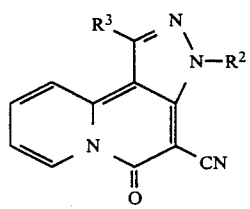

(IA)

where $R^2$ and $R^3$ are as previously defined are preferable, and the compounds wherein $R^3$ is a propyl group are more preferable. The most preferred compounds are 4-cyano-1-propyl-5H-pyrazolo[4,3-a]quinolizin-5-one and 3-acetyl-4-cyano-1-propyl-5H-pyrazolo[4,3-a]quinolizin-5one.

The 5H-pyrazolo[4,3-a]quinolizin-5-one derivatives of the formula (I) of this invention can be administered in various dosage forms depending upon the intended therapy. Typical dosage forms which can be used are tablets, pills, powder, liquid preparations, suspensions, emulsions, granules, capsules, suppositories, and injectable preparations.

In molding the pharmaceutical compositions into a tablet form, a wide variety of conventional carriers known in the art can be used. Examples of suitable carriers are excipients such as glucose, lactose, starch, cacao butter, hardened vegetable oils, kaolin and talc; binders such as gum arabic powder, tragacanth powder, and ethanol; and disintegrants such as laminaria and agar. The tablets, if desired, can be coated and made into sugar-coated tablets, gelatin-coated tablets, film-coated tablets, or tablets coated with two or more layers.

When a pharmaceutical composition is formulated into an injectable preparation, it is preferred that the resulting injectable solution and suspension are sterilized and rendered isotonic with respect to blood. In making the pharmaceutical composition into a solution or suspension, any diluents customarily used in the art can be employed. Examples of suitable diluents include water, ethyl alcohol, propylene glycol, polyoxyethylene sorbitol, and sorbitan esters. Sodium chloride, glucose or glycerol may be incorporated into a therapeutic agent in an amount sufficient to prepare an isotonic solution. The therapeutic agent may further contain ordinary dissolving aids, buffers, pain-alleviating agents, and preservatives, and optionally, coloring agents, fragrances, flavors, sweeteners, and other pharmacologically active agents.

The dosage of the quinolizinone derivatives of the present invention may be in a range from approximately 0.1 mg to 10 mg per kg of mammal weight for an oral administration, or from about 0.02 mg to 5 mg per kg of mammal weight for a parenteral administration, per day in multiple doses depending upon the type of mammal disease, the severity of condition to be treated, and the like.

This invention is further illustrated in more detail by way of the following examples and pharmacological data.

REFERENCE EXAMPLE 1

1-Butyryl-3-cyano-2-methylthio-4H -quinolizin-4-one (R-1)

A mixture of 56.1 g of propyl 2-pyridylmethyl ketone and 70.0 g of methyl 2-cyano-3,3-bismethylthioacrylate was stirred for 16 hours at 120° C. The mixture was chromatographed on silica gel column using a mixed solvent of dichloromethane and diethyl ether (5:1, v/v) as an eluent to give 50.3 g of 1-butyryl-3-cyano-2-methylthio-4H-quinolizin-4-one as pale yellow crystals.

$^1$H NMR (CDCl$_3$) δ: 1.04(t, 3H), 1.80(m, 2H), 2.73(s, 3H), 2.91(t, 2H), 7.33(dt, 1H), 7.53(d, 1H), 7.76(dt, 1H); 9.30(d, 1H).

REFERENCE EXAMPLE 2

The following compounds were obtained according to the same procedure as described in Reference Example 1.

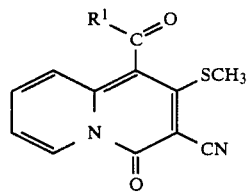

| Comp. No. | $R^1$ | $^1$H NMR (CDCl$_3$), δ |
|---|---|---|
| R-2 | CH$_3$— | 2.79(s,3H),2.84(s,3H),7.34(dt,1H),7.63(d,1H), 7.78(dt,1H), 9.30(d, 1H) |
| R-3 | CH$_3$CH$_2$— | 1.28(t,3H),2.73(s,3H),2.93(q,2H),7.33(t,1H),7.50(d,1H), 7.76(dt, 1H), 9.29(d, 1H) |
| R-4 | (CH$_3$)$_2$CH— | 1.23(d,6H),2.72(s,3H),3.31(m,1H),7.33(dt,1H),7.54(d,1H), 7.76(dt,1H),9.30(d,1H) |
| R-5 | CH$_3$(CH$_2$)$_3$— | 0.96(t,3H),1.44(m,2H),1.75(m,2H),2.72(s,3H),2.92(t,2H), 7.33(dt,1H),7.52(d,1H),7.76(dt,1H),9.30(d,1H) |
| R-6 | (CH$_3$)$_2$CHCH$_2$— | 1.05(d,6H),2.33(m,1H),2.73(s,3H),2.84(d,2H),7.33(dt,1H), 7.55(d,1H),7.77(dt,1H),9.30(d,1H) |
| R-7 | CH$_3$CH$_2$CH—<br>\|<br>CH$_3$ | 0.98(t,3H),1.22(d,3H),1.45(m,1H),1.79(m,1H),2.73(s,3H), 3.11(m,1H),7.33(t,1H),7.58(d,1H),7.75(dt,1H),9.30(d,1H) |

-continued

| Comp. No. | R¹ | ¹H NMR (CDCl₃), δ |
|---|---|---|
| R-8 | (CH₃)₃C— | 1.33(s,9H),2.71(s,3H),7.31(t,1H),7.37(d,1H),7.72(dt,1H), 9.28(d,1H) |
| R-9 | (CH₃)₂CH(CH₂)₂— | 0.96(d,6H),1.61–1.72(m,3H),2.73(s,3H),2.92(t,2H), 7.33(t,1H),7.54(d,1H),7.76(dt,1H),9.30(d,1H) |
| R-10 | (CH₃)₃CCH₂— | 1.16(s,9H),2.72(s,3H),2.87(s,2H),7.33(dt,1H),7.57(d,1H), 7.77(dt,1H),9.29(d,1H) |
| R-11 | CH₃(CH₂)₄— | 0.92(t,3H),1.33–1.42(m,4H),1.77(m,2H),2.73(s,3H),2.91(t, 2H),7.33(dt,1H),7.53(d,1H),7.76(dt,1H),9.30(d,1H) |
| R-12 | CH₃(CH₂)₅— | 0.90(t,3H),1.25–1.46(m,6H),1.76(m,2H),2.73(s,3H),2.92(t, 2H),7.33(dt,1H),7.53(d,1H),7.76(dt,1H),9.29(d,1H) |
| R-13 | CH₃(CH₂)₆— | 0.89(t,3H),1.23–1.43(m,8H),1.76(m,2H),2.71(s,3H),2.91(t, 2H),7.32(t,1H),7.53(d,1H),7.74(dt,1H),9.30(d,1H) |
| R-14 | CH₃(CH₂)₇— | 0.89(t,3H),1.22–1.45(m,10H),1.76(m,2H),2.72(s,3H),2.91(t, 2H),7.32(t,1H),7.53(d,1H),7.75(dt,1H),9.29(d,1H) |
| R-15 | CH₃(CH₂)₅CH—<br>           \|<br>           CH₃ | 0.87(t,3H),1.21(d,3H),1.17–1.36(br,8H),1.43(m,1H),1.72(m, 1H),2.72(s,3H),3.27(m,1H),7.33(dt,1H),7.58(d,1H),7.76(dt, 1H),9.30(d,1H) |
| R-16 |  | 2.57(s,3H),7.31(t,1H),7.45–7.55(m,3H),7.62–7.71(m,2H), 7.84(d,2H),9.33(d,1H) |
| R-17 | 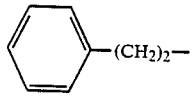—(CH₂)₂— | 2.68(s,3H),3.13(t,2H),3.26(t,2H),7.17–7.31(m,7H),7.60(dt, 1H),9.26(d,1H) |

EXAMPLE 1

4-Cyano-1-propyl-5H-pyrazolo[4,3-a]quinolizin-5-one (S-1)

To a solution of 212 g of 1-butyryl-3-cyano-2-methylthio-4H-quinolizin-4-one in 1.5 l of dimethyl sulfoxide were added 74 ml of hydrazine hydrate and the reaction mixture was stirred for 1 hour at room temperature.

To the reaction mixture was added 2 l of cold water and the precipitated crystals were collected by filtration and washed with water (1.0 l), ethyl alcohol (0.5 l) and diethyl ether (0.5 l) successively to give 144 g of 4-cyano-1-propyl-5H-pyrazolo[4,3-a]quinolizin-5-one as pale yellow crystals.

Melting point: 298°–300° C.
IR (KBr): 2205, 1670, 1625, 1605 cm⁻¹
¹H NMR (DMSO-d₆) δ: 1.12(t, 3H), 1.89(m, 2H), 3.17(t, 2H), 7.78(t, 1H), 8.38(m, 2H), 9.50(d, 1H), 13.46(br, 1H).
Elementary analysis: $C_{14}H_{12}N_4O$

|  | C % | H % | N % |
|---|---|---|---|
| Calcd. | 66.65 | 4.79 | 22.21 |
| Found | 66.78 | 4.81 | 22.21 |

EXAMPLE 2

The following compounds were obtained according to the same procedure as described in Example 1.

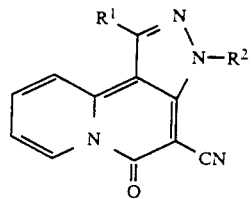

| Comp. No. | R¹ | R² | melting point (°C.) | IR (KBr cm⁻¹) | ¹H-NMR (DMSO-d₆), δ | Elementary analysis | C% | H% | N% |
|---|---|---|---|---|---|---|---|---|---|
| S-2 | CH₃— | H | >300 | 3275 2210 1660 1620 1600 | 2.78(s,3H), 7.77(t, 1H),8.34–8.46(m, 2H),9.49(d,1H) 13.43(br,1H) | $C_{12}H_8N_4O$<br>Calcd.<br>Found | 64.75<br>64.66 | 3.60<br>3.67 | 24.99<br>25.25 |
| S-3 | CH₃CH₂— | H | >300 | 3240 2235 1670 1630 1610 | 1.67(t,3H),3.41(q, 2H),7.98(dt,1H), 8.59(m,2H),9.72(d, 1H),13.65(br,1H) | $C_{13}H_{10}N_4O$<br>Calcd.<br>Found | 65.54<br>65.70 | 4.23<br>4.32 | 23.52<br>23.02 |
| S-4 | (CH₃)₂CH— | H | 259–261 | 3280 2205 1675 1655 1625 | 1.38(d,6H),3.58(m, 1H),7.67(dt,1H), 8.30(m,2H),9.43(d, 1H),13.33(br,1H) | $C_{14}H_{12}N_4O$<br>Calcd.<br>Found | 66.65<br>66.73 | 4.79<br>4.84 | 22.21<br>22.09 |
| S-5 | CH₃(CH₂)₃— | H | 249 | 1600 3225 | 0.93(t,3H),1.46(m, | $C_{15}H_{14}N_4O$ | | | |

-continued

| Comp. No. | R¹ | R² | melting point (°C.) | IR (KBr cm⁻¹) | ¹H-NMR (DMSO-d₆), δ | Elementary analysis | C% | H% | N% |
|---|---|---|---|---|---|---|---|---|---|
| | | | | 2205<br>1665<br>1630<br>1605 | 2H),1.73(m,2H),3.06<br>(t,2H),7.66(dt,1H),<br>8.25(m,2H),9.41(d,<br>1H),13.35(br,1H) | Calcd.<br>Found | 67.65<br>67.75 | 5.30<br>5.35 | 21.04<br>21.06 |
| S-6 | (CH₃)₂CHCH₂— | H | 286–288 | 3300<br>2200<br>1675<br>1655<br>1620<br>1600 | 1.00(d,6H),2.10(m,<br>1H),2.95(d,2H),7.67<br>(t,1H),8.22–8.32<br>(m,2H),9.40(d,1H),<br>13.35(br,1H) | $C_{15}H_{14}N_4O$<br>Calcd.<br>Found | 67.65<br>67.91 | 5.30<br>5.29 | 21.04<br>21.20 |
| S-7 | CH₃CH₂CH—<br>\|<br>CH₃ | H | 291–293 | 3320<br>3280<br>2200<br>1665<br>1625<br>1600 | 0.95(t,3H),1.33(d,<br>3H),1.64(m,1H),1.93<br>(m,1H),3.40(m,1H),<br>7.67(dt,1H),8.30(m,<br>2H),9.43(d,1H),<br>13.36(br,1H) | $C_{15}H_{14}N_4O$<br>Calcd.<br>Found | 67.65<br>67.48 | 5.30<br>5.29 | 21.04<br>21.08 |
| S-8 | (CH₃)₃C— | H | >300 | 3220<br>2205<br>1680<br>1630<br>1595 | 1.55(s,9H),7.69(t,<br>1H),8.36(t,1H),8.52<br>(d,1H),9.50(d,1H),<br>13.34(br,1H) | $C_{15}H_{14}N_4O$<br>Calcd.<br>Found | 67.65<br>67.61 | 5.30<br>5.23 | 21.04<br>20.73 |
| S-9 | (CH₃)₂CH(CH₂)₂— | H | 221 | 3230<br>2205<br>1670<br>1630<br>1605 | 1.09(d,6H),1.71–<br>1.88(m,3H),3.17(t,<br>2H),7.78(t,1H),8.32–<br>8.45(m,2H),9.51(d,<br>1H),13.46(br,1H) | $C_{16}H_{16}N_4O$<br>Calcd.<br>Found | 68.55<br>68.38 | 5.75<br>5.78 | 19.99<br>19.87 |
| S-10 | (CH₃)₃CCH₂— | H | 278–280 | 2205<br>1650<br>1625<br>1600 | 1.02(s,9H),3.19(s,<br>2H), 7.67(t,1H),8.27<br>(t,1H),8.56(d,1H),<br>9.44(d,1H),13.43(br,<br>1H) | $C_{16}H_{16}N_4O$<br>Calcd.<br>Found | 68.55<br>68.54 | 5.75<br>5.82 | 19.99<br>19.82 |
| S-11 | CH₃(CH₂)₄— | H | 240–242 | 2210<br>1675<br>1625<br>1605 | 0.90(t,3H),1.39 (m,<br>4H),1.76(m,2H),3.05<br>(t,2H),7.66(t,1H),<br>8.21–8.34(m,2H),<br>9.40(d,1H),13.33(br,<br>1H) | $C_{16}H_{16}N_4O$<br>Calcd.<br>Found | 68.55<br>68.08 | 5.75<br>5.80 | 19.99<br>19.99 |
| S-12 | CH₃(CH₂)₅— | H | 215 | 3310<br>2200<br>1670<br>1625<br>1605 | 0.88(t,3H),1.32(m,<br>4H),1.45(m,2H),1/75<br>(m,2H),3.05(t,2H),<br>7.65(t,1H),8.22–<br>8.32(m,2H),9.40(d,<br>1H0,13.31(br,1H) | $C_{17}H_{18}N_4O$<br>Calcd.<br>Found | 69.37<br>68.08 | 6.16<br>6.20 | 19.03<br>18.74 |
| S-13 | CH₃(CH₂)₆— | H | 220–222 | 3310<br>2210<br>1680<br>1665<br>1625<br>1600 | 0.87(t,3H),1.22–<br>1.48(m,8H),1.75(m,<br>2H),3.06(t,2H),7.67<br>(t,1H),8.25–8.34<br>(m,2H),9.41(d,1H),<br>13.32(br,1H) | $C_{18}H_{20}N_4O$<br>Calcd.<br>Found | 70.11<br>69.70 | 6.54<br>6.65 | 18.17<br>18.28 |
| S-14 | CH₃(CH₂)₇— | H | 196–198 | 3300<br>2200<br>1670<br>1660<br>1615<br>1600 | 0.85(t,3H),1.19–<br>1.50(m,10H),1.74(m,<br>2H0,3.04(t,2H),7.67<br>(t,1H),8.26(m,2H),<br>9.40(d,1H),13.32(br,<br>1H) | $C_{19}H_{22}N_4O$<br>Calcd.<br>Found | 70.78<br>70.85 | 6.88<br>6.95 | 17.38<br>17.56 |
| S-15 | CH₃<br>\|<br>CH₃(CH₂)₅CH— | H | 157–158 | 3325<br>2200<br>1660<br>1620<br>1595 | 0.83(t,3H),1.15–<br>1.45(br,6H),1.32(d,<br>3H),1.59(m,2H),1.91<br>(m,2H),3.44(m,1H),<br>7.66(t,1H),8.30(brs,<br>2H),9.42(d,1H),<br>13.34(br,1H) | $C_{19}H_{22}N_4O$<br>Calcd.<br>Found | 70.78<br>70.66 | 6.88<br>6.98 | 17.38<br>17.41 |
| S-16 | phenyl | H | >300 | 3220<br>2210<br>1665<br>1625<br>1600 | 7.64–7.81(m,6H),<br>8.00(d,1H),8.27(t,<br>1H),9.53(d,1H),<br>13.92(br,1H), | $C_{17}H_{10}N_4O$<br>Calcd.<br>Found | 71.32<br>70.93 | 3.52<br>3.40 | 19.57<br>18.99 |
| S-17 | phenyl-(CH₂)₂— | H | 270–273 | 3210<br>2205<br>1670<br>1655<br>1620<br>1600 | 3.11(t,2H),3.36(t,<br>2H),7.16–7.36(m,<br>5H),7.66(dt,1H),<br>8.28(m,2H),9.40(d,<br>1H),13.38(br,1H) | $C_{19}H_{14}N_4O$<br>Calcd.<br>Found | 72.60<br>72.75 | 4.49<br>4.42 | 17.82<br>17.73 |
| S-18 | CH₃— | CH₃ | 299–300 | 2200<br>1670<br>1625 | 2.77(s,3H),4.16(s,<br>3H),7.78(dt,1H),<br>8.36–8.46(m,2H),<br>9.48(d,1H) | $C_{13}H_{10}N_4O$<br>Calcd.<br>Found | 65.54<br>65.80 | 4.23<br>4.36 | 23.52<br>23.69 |

-continued

| Comp. No. | R¹ | R² | melting point (°C.) | IR (KBr cm⁻¹) | ¹H-NMR (DMSO-d₆), δ | Elementary analysis | | | |
|---|---|---|---|---|---|---|---|---|---|
| | | | | | | | C% | H% | N% |
| S-19 | CH₃— | phenyl | >300 | 2205, 1675, 1620 | 2.94(s,3H),7.68–7.80(m,5H),7.97(dt, 1H),8.56(dt,1H), 8.62(d,1H),9.74(d, 1H) | C₁₈H₁₂N₄O Calcd. Found | 71.99 71.63 | 4.03 4.09 | 18.66 18.61 |
| S-20 | CH₃CH₂— | CH₃— | >300 | 2195, 1660, 1615 | (CDCl₃):w 1.45(t,3H),3.09(q, 2H),4.20(s,3H),7.43 (dt,1H),8.02(dt, 1H),8.09(d,1H),9.55 (d,1H) | C₁₄H₁₂N₄O Calcd. Found | 66.65 66.55 | 4.79 4.85 | 22.21 22.49 |
| S-21 | Ch₃CH₂— | phenyl | >300 | 2200, 1660, 1620 | 1.37(t,3H),3.27(q, 2H),7.76(m,5H),7.99 (dt,1H),8.57(m,2H), 9.77(d,1H) | C₁₉H₁₄N₄O Calcd. Found | 72.60 72.66 | 4.49 4.48 | 1782. 17.63 |
| S-22 | CH₃(CH₂)₂— | CH₃— | 265.5–266 | 2200, 1660, 1620 | 1.14(t,3H),1.88(m, 2H),3.12(t,2H),4.18 (s,3H),7.79(dt,1H), 8.33–8.46(m,2H), 9.50(d,1H) | C₁₅H₁₄N₄O Calcd. Found | 67.65 67.47 | 5.30 5.32 | 21.04 20.83 |
| S-23 | CH₃(CH₂)₂— | phenyl | >300 | 2195, 1670, 1615 | 0.97(t,3H),1.76(m, 2H),3.26(t,2H),7.70–7.82(m,5H),7.99 (dt,1H),8.51–8.63 (m,2H),9.78(d,1H) | C₂₀H₁₆N₄O Calcd. Found | 73.15 72.83 | 4.91 4.91 | 17.06 16.76 |
| S-24 | phenyl | CH₃— | 260–262 | 2200, 1675, 1625 | (CDCl₃):δ 4.31(s,3H),7.42(dt, 1H),7.53–7.63(m, 5H),7.78(dt,1H), 7.94(d,1H),9.56(d, 1H) | C₁₈H₁₂N₄O Calcd. Found | 71.99 71.91 | 4.03 3.89 | 18.66 18.55 |
| S-25 | phenyl-(CH₂)₂— | CH₃— | 199–201 | 2200, 1670, 1625 | (CDCl₃): δ 3.20(m,2H),3.35(m, 2H),4.23(s,3H),7.22–7.35(m,5H),7.42 (dt,1H),7.97(dt, 1H),8.04(d,1H),9.55 (d,1H) | C₂₀H₁₆N₄O Calcd. Found | 73.15 73.03 | 4.91 4.85 | 17.06 1693 |

EXAMPLE 3

3-Acetyl-4-cyano-1-propyl-5H-pyrazolo[4,3-a]quinolizin-5-one (S-26)

A mixture of 80 g of 4-cyano-1-propyl-5H-pyrazolo-[4,3-a]quinolizin-5-one (S-1) and 2.0 l of acetic anhydride was heated under reflux for 18 hours. The solvent was evapolated under reduced pressure and the residual crystals were washed with water (0.5 l), methyl alcohol (0.5 l) and chloroform (0.5 l) successively to give 84 g of 3-acetyl-4-cyano-1-propyl-5H-pyrazolo-[4,3-a]quinolizin-5-one as pale yellow crystals.

Melting point: 269°–270.5° C.

IR (KBr): 2210, 1735, 1670, 1625 cm⁻¹

¹H-NMR (DMSO-d₆) δ: 1.20(t, 3H), 1.97(m, 2H), 2.84(s, 3H), 3.22(t, 2H), 7.89(dt, 1H), 8.47(dt, 1H), 8.50(d, 1H); 9.55(d, 1H).

Elementary analysis: C₁₆H₁₄N₄O₂

|  | C % | H % | N % |
|---|---|---|---|
| Calcd. | 65.30 | 4.79 | 19.04 |
| Found | 65.53 | 4.73 | 18.88 |

EXAMPLE 4

The following compounds were obtained according to the same procedure as described in Example 3.

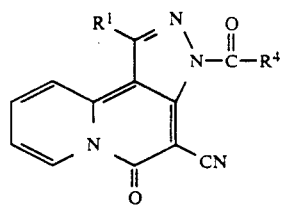

| Comp. No. | R¹ | R⁴ | melting point (°C.) | IR (KBr cm⁻¹) | ¹H-NMR (DMSO-d₆), δ | Elementary analysis | | | |
|---|---|---|---|---|---|---|---|---|---|
| | | | | | | | C % | H % | N % |
| S-27 | CH₃(CH₂)₂— | CH₃CH₂— | 257–260 | 2210, 1735, 1660, 1620 | 1.20(t, 3H), 1.35(t, 3H), 1.97(m, 2H), 3.21–3.34(m, 4H), 7.89 (dt, 1H), 8.43–8.54 (m, 2H), 9.57(d, 1H) | C₁₇H₁₆N₄O₂ Calcd. Found | 66.22 66.08 | 5.23 5.17 | 18.17 18.05 |

-continued

| Comp. No. | R¹ | R⁴ | melting point (°C.) | IR (KBr cm⁻¹) | ¹H-NMR (DMSO-d₆), δ | Elementary analysis | | | |
|---|---|---|---|---|---|---|---|---|---|
| S-28 | $CH_3(CH_2)_2-$ |  | 250–252 | 2210 1700 1665 1625 | 1.01(t, 3H), 1.86(m, 2H), 3.08(t, 2H), 7.60–7.85(m, 4H), 8.06(d, 2H), 8.36–8.46(m, 2H), 9.50(d, 1H) | $C_{21}H_{16}N_4O_2$ Calcd. Found | C % 70.78 70.71 | H % 4.53 4.42 | N % 15.72 15.66 |
| S-29 | $CH_3-$ | $CH_3-$ | 268–270 | 2210 1735 1665 1615 | 2.71(s, 3H), 2.75(s, 3H), 7.78(dt, 1H), 8.34(dt, 1H), 8.47(d, 1H), 9.44(d, 1H) | $C_{14}H_{10}N_4O_2$ Calcd. Found | C % 63.15 63.05 | H % 3.79 3.75 | N % 21.04 20.94 |
| S-30 | $CH_3-$ |  | 295–298 | 2225 1710 1660 1620 | 2.71(s, 3H), 7.62(t, 2H), 7.74(d, 1H), 7.81(dt, 1H), 8.03(d, 2H), 8.38(dt, 1H), 8.50(d, 1H), 9.50(d, 1H) | $C_{18}H_{12}N_4O_2$ Calcd. Found | C % 68.35 68.02 | H % 3.82 3.55 | N % 17.71 17.52 |
| S-31 | $CH_3CH_2-$ | $CH_3-$ | 293–295 | 2215 1735 1665 1615 | 1.37(t, 3H), 2.71(s, 3H), 3.16(q, 2H), 7.79 (dt, 1H), 8.35(dt, 1H), 8.43(d, 1H), 9.45 (d, 1H) | $C_{15}H_{12}N_4O_2$ Calcd. Found | C % 64.28 64.29 | H % 4.32 4.23 | N % 19.99 19.88 |
| S-32 | $CH_3CH_2-$ | $CH_3CH_2-$ | 294–196 | 2215 1735 1665 1620 | 1.20(t, 3H), 1.37(t, 3H), 3.13–3.25(m, 4H), 7.79(dt, 1H), 8.34(dt, 1H), 8.42(d, 1H), 9.45(d, 1H) | $C_{16}H_{14}N_4O_2$ Calcd. Found | C % 65.30 65.45 | H % 4.79 4.71 | N % 19.04 18.94 |
| S-33 | $CH_3CH_2-$ |  | 293–295 | 2210 1700 1665 1625 | 1.30(t, 3H), 3.16(q, 2H), 7.63(t, 2H), 7.75 (d, 1H), 7.82(dt, 1H), 8.07(d, 2H), 8.40(dt, 1H), 8.46(d, 1H), 9.52 (d, 1H) | $C_{19}H_{14}N_4O_2$ Calcd. Found | C % 69.08 69.49 | H % 4.27 3.99 | N % 16.96 16.68 |
| S-34 | $(CH_3)_2CH-$ | $CH_3-$ | 236–238 | 2210 1735 1660 1620 | 1.40(d, 6H), 2.72(s, 3H), 3.65(m, 1H), 7.78 (dt, 1H), 8.36(dt, 1H), 8.43(d, 1H), 9.46 (d, 1H) | $C_{16}H_{14}N_4O_2$ Calcd. Found | C % 65.30 65.56 | H % 4.79 4.79 | N % 19.04 19.20 |
| S-35 | $(CH_3)_2CH-$ | $CH_3CH_2-$ | 239–241 | 2220 1730 1665 1615 | 1.21(t, 3H), 1.40(d, 6H), 3.20(q, 2H), 3.68 (m, 1H), 7.78(dt, 1H), 8.36(dt, 1H), 8.43(d, 1H), 9.46(d, 1H) | $C_{17}H_{16}N_4O_2$ Calcd. Found | C % 66.22 66.57 | H % 5.23 5.15 | N % 18.17 18.06 |
| S-36 | $CH_3(CH_2)_3-$ | $CH_3-$ | 215–216 | 2210 1740 1665 1620 | 0.98(t, 3H), 1.51(m, 2H), 1.78(m, 2H), 2.71 (s, 3H), 3.12(t, 2H), 7.78(dt, 1H), 8.31–8.43(m, 2H), 9.46(d, 1H) | $C_{17}H_{16}N_4O_2$ Calcd. Found | C % 66.22 65.80 | H % 5.23 5.26 | N % 18.17 18.15 |
| S-37 | $CH_3(CH_2)_3-$ | $CH_3CH_2-$ | 237–238 | 2210 1745 1660 1615 | 1.09(t, 3H), 1.32(t, 3H), 1.63(m, 2H), 1.89 (m, 2H), 3.21–3.34 (m, 4H), 7.90(dt, 1H), 8.47–8.56(m, 2H), 9.57(d, 1H) | $C_{18}H_{18}N_4O_2$ Calcd. Found | C % 67.07 66.69 | H % 5.63 5.64 | N % 17.38 17.13 |
| S-38 | $(CH_3)_2CHCH_2-$ | $CH_3-$ | 238–240 | 2220 1740 1655 1615 | 1.17(d, 6H), 2.29(m, 1H), 2.84(s, 3H), 3.13 (d, 2H), 7.91(m, 1H), 8.51(m, 2H), 9.57(d, 1H) | $C_{17}H_{16}N_4O_2$ Calcd. Found | C % 66.22 66.06 | H % 5.23 5.18 | N % 18.17 18.05 |
| S-39 | $(CH_3)_2CHCH_2-$ | $CH_3CH_2-$ | 236 | 2205 1730 1665 1620 | 1.05(d, 6H), 1.20(t, 3H), 2.17(m, 1H), 3.00 (d, 2H), 3.17(q, 2H), 7.78(m, 1H), 8.32–8.40(m, 2H), 9.45(d, 1H) | $C_{18}H_{18}N_4O_2$ Calcd. Found | C % 67.07 66.88 | H % 5.63 5.66 | N % 17.38 17.42 |
| S-40 | $CH_3CH_2\underset{\underset{CH_3}{\mid}}{CH}-$ | $CH_3-$ | 190–192 | 2220 1740 1665 1615 | 1.01(t, 3H), 1.38(d, 3H), 1.64(m, 1H), 1.98 (m, 1H), 2.71(s, 3H), 3.50(m, 1H), 7.78(dt, 1H), 8.37(dt, 1H), 8.42(d, 1H), 9.48(d, 1H) | $C_{17}H_{16}N_4O_2$ Calcd. Found | C % 66.22 66.03 | H % 5.23 5.22 | N % 18.17 18.03 |

-continued

| Comp. No. | $R^1$ | $R^4$ | melting point (°C.) | IR (KBr cm$^{-1}$) | $^1$H-NMR (DMSO-d$_6$), δ | Elementary analysis | | | |
|---|---|---|---|---|---|---|---|---|---|
| S-41 | CH$_3$CH$_2$CH— \| CH$_3$ | CH$_3$CH$_2$— | 200-210 | 2210 1730 1660 1620 | 1.00(t, 3H), 1.22(t, 3H), 1.37(d, 3H), 1.66 (m, 1H), 1.97(m, 1H), 3.18(q, 1H), 3.49(m, 1H), 7.78(dt, 1H), 8.36(dt, 1H), 8.42(d, 1H), 9.47(d, 1H) | C$_{18}$H$_{18}$N$_4$O$_2$ Calcd. Found | C % 67.07 66.85 | H % 5.63 5.67 | N % 17.38 17.29 |
| S-42 | (CH$_3$)$_3$C— | CH$_3$— | 287-289 | 2220 1735 1670 1625 | 1.58(s, 9H), 2.73(s, 3H), 7.82(dt, 1H), 8.44(dt, 1H), 8.62(d, 1H), 9.54(d, 1H) | C$_{17}$H$_{16}$N$_4$O$_2$ Calcd. Found | C % 66.22 65.97 | H % 5.23 5.19 | N % 18.17 17.99 |
| S-43 | (CH$_3$)$_3$C— | CH$_3$CH$_2$— | 278-280 | 2220 1735 1670 1620 | 1.22(t, 3H), 1.58(s, 9H), 3.21(q, 2H), 7.82 (t, 1H), 8.44(dt, 1H), 8.61(d, 1H), 9.54(d, 1H) | C$_{18}$H$_{18}$N$_4$O$_2$ Calcd. Found | C % 67.07 67.06 | H % 5.63 5.67 | N % 17.38 17.25 |
| S-44 | (CH$_3$)$_2$CH(CH$_2$)$_2$— | CH$_3$— | 209-210 | 2205 1740 1665 1615 | 1.00(d, 6H), 1.64–1.83(m, 3H), 2.71(s, 3H), 31.3(t, 2H), 7.80 (m, 1H), 8.39(m, 2H), 9.46(d, 1H) | C$_{18}$H$_{18}$N$_4$O$_2$ Calcd. Found | C % 67.07 67.54 | H % 5.63 5.66 | N % 17.38 16.84 |
| S-45 | (CH$_3$)$_2$CH(CH$_2$)$_2$— | CH$_3$CH$_2$— | 241-242 | 2225 1750 1670 1625 | 1.00(d, 6H), 1.20(t, 3H), 1.65–1.80(m, 3H), 3.09–3.26(m, 4H), 7.81(dt, 1H), 8.36–8.40(m, 2H), 9.46(d, 1H) | C$_{19}$H$_{20}$N$_4$O$_2$ Calcd. Found | C % 67.84 67.11 | H % 5.99 6.03 | N % 16.66 16.36 |
| S-46 | (CH$_3$)$_3$CCH$_2$— | CH$_3$— | 264-266 | 2210 1740 1655 1615 | 1.08(s, 9H), 2.71(s, 3H), 3.09(s, 2H), 7.78 (dt, 1H), 8.34(t, 1H), 8.65(d, 1H), 9.46(d, 1H) | C$_{18}$H$_{18}$N$_4$O$_2$ Calcd. Found | C % 67.07 67.51 | H % 5.63 5.67 | N % 17.38 17.23 |
| S-47 | (CH$_3$)$_3$CCH$_2$— | CH$_3$CH$_2$— | 268-270 | 2210 1735 1665 1620 | 1.08(s, 9H), 1.22(t, 3H), 3.08(s, 2H), 3.18 (q, 2H), 7.78(dt, 1H), 8.33(dt, 1H), 8.65(d, 1H), 9.47(d, 1H) | C$_{19}$H$_{20}$N$_4$O$_2$ Calcd. Found | C % 67.84 67.77 | H % 5.99 6.04 | N % 16.66 16.71 |
| S-48 | CH$_3$(CH$_2$)$_4$— | CH$_3$— | 200-202 | 2205 1730 1660 1615 | 0.91(t, 3H), 1.33–1.53(m, 4H), 1.80(m, 2H), 2.72(s, 3H), 3.12 (t, 2H), 7.78(dt, 1H), 8.32–8.42(m, 2H), 9.44(d, 1H) | C$_{18}$H$_{18}$N$_4$O$_2$ Calcd. Found | C % 67.07 66.99 | H % 5.63 5.66 | N % 17.38 17.31 |
| S-49 | CH$_3$(CH$_2$)$_4$— | CH$_3$CH$_2$— | 228-230 | 2210 1730 1655 1615 | 0.90(t, 3H), 1.20(t, 3H), 1.34–1.53(m, 4H), 1.80(m, 2H), 3.09–3.22(m, 4H), 7.78 (dt, 1H), 8.36(t, 1H), 8.39(d, 1H), 9.45(d, 1H) | C$_{19}$H$_{20}$N$_4$O$_2$ Calcd. Found | C % 67.84 67.51 | H % 5.99 6.00 | N % 16.66 16.84 |
| S-50 | CH$_3$(CH$_2$)$_5$— | CH$_3$— | 221-222 | 2200 1725 1650 1615 | 0.89(t, 3H), 1.33(m, 4H), 1.49(m, 2H), 1.78 (m, 2H), 2.70(s, 3H), 3.12(t, 2H), 7.78(dt, 1H), 8.32–8.43(m, 2H), 9.46(d, 1H) | C$_{19}$H$_{20}$N$_4$O$_2$ Calcd. Found | C % 67.84 67.70 | H % 5.99 5.98 | N % 16.66 16.35 |
| S-51 | CH$_3$(CH$_2$)$_5$— | CH$_3$CH$_2$— | 243-244 | 2210 1730 1655 1615 | (CDCl$_3$): δ 0.93(t, 3H), 1.25–1.59(m, 9H), 1.87(m, 2H), 3.07(t, 2H), 3.21 (q, 2H), 7.52(dt, 1H), 8.06(dt, 1H), 8.18(d, 1H), 9.60(d, 1H) | C$_{20}$H$_{22}$N$_4$O$_2$ Calcd. Found | C % 68.55 68.16 | H % 6.33 6.40 | N % 15.99 15.82 |
| S-52 | CH$_3$(CH$_2$)$_6$— | CH$_3$— | 200-202 | 2225 1740 1680 1630 | 0.88(t, 3H), 1.24–1.54(m, 8H), 1.79(m, 2H), 2.72(s, 3H), 3.12 (t, 2H), 7.78(dt, 1H), 8.31–8.41(m, 2H), 9.45(d, 1H) | C$_{20}$H$_{22}$N$_4$O$_2$ Calcd. Found | C % 68.55 68.13 | H % 6.33 6.36 | N % 15.99 15.77 |
| S-53 | CH$_3$(CH$_2$)$_6$— | CH$_3$CH$_2$— | 233-235 | 2220 1735 1660 1620 | 0.87(t, 3H), 1.22(t, 3H), 1.24–1.54(m, 8H), 1.80(m, 2H), 3.09–3.21(m, 4H), 7.77 (dt, 1H), 8.29–8.40 (m, 2H), 9.44(d, 1H) | C$_{21}$H$_{24}$N$_4$O$_2$ Calcd. Found | C % 69.21 69.07 | H % 6.64 6.67 | N % 15.37 15.30 |
| S-54 | CH$_3$(CH$_2$)$_7$— | CH$_3$— | 216-218 | 2200 | (CDCl$_3$): δ | C$_{21}$H$_{24}$N$_4$O$_2$ | | | |

-continued

| Comp. No. | R¹ | R⁴ | melting point (°C.) | IR (KBr cm⁻¹) | ¹H-NMR (DMSO-d₆), δ | Elementary analysis | | | |
|---|---|---|---|---|---|---|---|---|---|
| | | | | 1720 1650 1610 | 0.90(t, 3H), 1.23-1.43(m, 8H), 1.53(m, 2H), 1.87(m, 2H), 2.75 (s, 3H), 3.07(t, 2H), 7.54(dt, 1H), 8.09(dt, 1H), 8.19(d, 1H), 9.56 d, 1H) | Calcd. Found | C % 69.21 68.76 | H % 6.64 6.65 | N % 15.37 15.34 |
| S-55 | $CH_3(CH_2)_7$— | $CH_3CH_2$— | 249-251 | 2210 1735 1655 1620 | (CDCl₃): δ 0.89(t, 3H), 1.34(t, 3H), 1.22-1.56(m, 12H), 1.87(m, 2H), 3.06(t, 2H), 3.20(q, 2H), 7.52(t, 1H), 8.07 (t, 1H), 8.18(d, 1H), 9.58(d, 1H) | $C_{22}H_{26}N_4O_2$ Calcd. Found | C % 69.82 69.78 | H % 6.92 7.13 | N % 14.80 14.74 |
| S-56 | $CH_3(CH_2)_5\underset{\underset{CH_3}{\vert}}{CH}$— | $CH_3$— | 146-148 | 2210 1740 1665 1615 | 0.85(t, 3H), 1.21-1.50(m, 8H), 1.37(d, 3H), 1.62(m, 1H), 1.96 (m, 1H), 2.71(s, 3H), 3.54(q, 1H), 7.79(t, 1H), 8.36(t, 1H), 8.42 (d, 1H), 9.47(d, 1H) | $C_{21}H_{24}N_4O_2$ Calcd. Found | C % 69.21 68.86 | H % 6.64 6.69 | N % 15.37 15.44 |
| S-57 | $CH_3(CH_2)_5\underset{\underset{CH_3}{\vert}}{CH}$— | $CH_3CH_2$— | 190-192 | 2210 1730 1665 1615 | 0.84(t, 3H), 1.19(t, 3H), 1.37(d, 3H), 1.15-1.49(m, 8H), 1.62(m, 1H), 1.94(m, 1H), 3.18 (q, 2H), 3.53(q, 1H), 7.78(dt, 1H), 8.32-8.46(m, 2H), 9.48(d, 1H) | $C_{22}H_{26}N_4O_2$ Calcd. Found | C % 69.82 69.89 | H % 6.92 7.01 | N % 14.80 14.81 |
| S-58 | 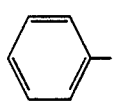 | $CH_3$— | 282-284 | 2210 1735 1660 1625 | 2.74(s, 3H), 7.62-7.74(m, 5H), 7.77(d, 2H), 8.16(t, 1H), 9.46 (d, 1H) | $C_{19}H_{12}N_4O_2$ Calcd. Found | C % 69.50 69.49 | H % 3.68 3.66 | N % 17.07 17.31 |
| S-59 | 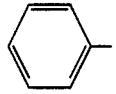 |  | 280-282 | 2220 1715 1665 1625 | 7.68-7.68(m, 10H), 8.11(d, 2H), 8.21(t, 1H), 9.51(d, 1H) | $C_{24}H_{14}N_4O_2$ Calcd. Found | C % 73.84 73.81 | H % 3.61 3.56 | N % 14.35 14.10 |
| S-60 | 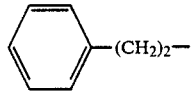 | $CH_3$— | 272-274 | 2210 1740 1670 1625 | 2.69(s, 3H), 3.17(t, 2H), 3.46(t, 2H), 7.18-7.40(m, 5H), 7.78 (dt, 1H), 8.34(dt, 1H), 8.42(d, 1H), 9.44 (d, 1H) | $C_{21}H_{16}N_4O_2$ Calcd. Found | C % 70.78 70.74 | H % 4.53 4.42 | N % 15.72 15.49 |
| S-61 | 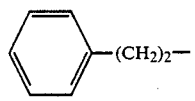 | 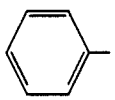 | 223-14 225 | 2220 1705 1670 1625 | 3.07(t, 2H), 3.46(t, 2H), 7.19-7.32(m, 5H), 7.57(t, 2H), 7.71-7.92(m, 4H), 8.39(t, 1H), 8.49(d, 1H), 9.50 (d, 1H) | $C_{26}H_{18}N_4O_2$ Calcd. Found | C % 74.63 74.47 | H % 4.34 4.26 | N % 13.39 13.12 |

TEST EXAMPLE

Determination of Igs produced in in vitro culture

BALB/c mice were immunized intraperitoneally with 5 μg of DNP-As adsorbed on 4 mg aluminum hydroxide gel. Four weeks after the immunization, the spleens were excised from the mice and $5 \times 10^7$ spleen cells were transferred intravenously into the recipient mice which had been exposed to 600 rad of X-ray irradiation. Immediately after the cell transfer, the recipients were then immunized intraperitoneally with 5 μg of DNP-As adsorbed on 4 mg aluminum hydroxide gel to induce adoptive secondary immune response. Further 4 weeks after the immunization of recipients, the spleens were excised from them and the spleen cell suspensions containing $5 \times 10^6$ cells/ml were cultured with or without a compound to be tested in 96-well micro-titer plates at 37° C. for 4 days. IgE and IgG secreted into the culture supernatant was each determined correspondingly by enzyme-linked immunosolvent assay and the inhibitory effect was calculated according to the following equation.

$$\text{inhibition \%} = \frac{\text{average amount of } Ig \text{ in control group} - \text{average amount of } Ig \text{ in test group}}{\text{average amount of } Ig \text{ in control group}} \times 100$$

The results obtained were shown below:

| Comp. No. | Concentration (μg/ml) | Inhibition % of IgE | Inhibition % of IgG |
| --- | --- | --- | --- |
| S-26 | 10 | 55 | 18 |
| S-31 | 20 | 75 | 33 |
| S-38 | 10 | 40 | 4 |

We claim:

1. 5H-pyrazolo[4,3-a]quinolizin-5-one compounds corresponding to the formula:

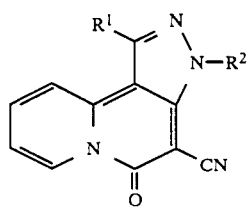

where $R^1$ is an alkyl group having 1 to 10 carbon atoms, a phenyl group, or a phenylalkyl group having 7 to 10 carbon atoms; $R^2$ is a hydrogen atom, an alkyl group having 1 to 3 carbon atoms, a phenyl group, an aliphatic acyl group having 2 to 6 carbon atoms, or a benzoyl group.

2. 5H-pyrazolo[4,3-a]quinolizin-5-one compounds corresponding to the formula:

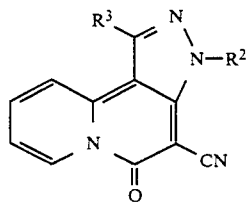

where $R^2$ is a hydrogen atom, an alkyl group having 1 to 3 carbon atoms, a phenyl group, an aliphatic acyl group having 2 to 6 carbon atoms, or a benzoyl group; and $R^3$ is an alkyl group having 1 to 4 carbon atoms.

3. 5H-pyrazolo[4,3-a]quinolizin-5-one compounds corresponding to the formula:

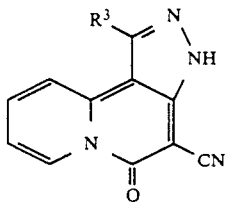

where $R^3$ is an alkyl group having 1 to 4 carbon atoms.

4. 5H-pyrazolo[4,3-a]quinolizin-5-one compounds corresponding to the formula:

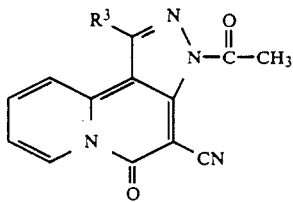

where $R^3$ is an alkyl group having 1 to 4 carbon atoms.

5. 4-Cyano-1-propyl-5H-pyrazolo[4,3-a]quinolizin-5-one.

6. 3-Acetyl-4-cyano-1-propyl-5H-pyrazolo[4,3-a]quinolizin-5-one.

7. A method for the treatment of allergic bronchial asthma, allergic rhinitis, atopic dermatitis and hypersensitiveness diseases associated with immunoglobulin E-antibody formation in a mammal which comprises administering an effective dosage from about 0.1 mg to 10 mg per kg of mammal weight by oral administration or from about 0.02 mg to 5 mg per kg of mammal weight by parenteral administration per day of an immunoglobulin E-antibody formation-inhibiting 5H-pyrazolo[4,3-a]quinolizin-5-one compound to the mammal; wherein the compound corresponds to the formula represented in claim 1, or a pharmaceutically acceptable salt thereof.

* * * * *

UNITED STATES PATENT AND TRADEMARK OFFICE
CERTIFICATE OF CORRECTION

PATENT NO. : 4,940,715

DATED : July 10, 1990

INVENTOR(S) : Kurashina et al

It is certified that error appears in the above-identified patent and that said Letters Patent is hereby corrected as shown below:

Col. 1, Title, "[4,3-A]" should be --[4,3-a]--.

Col. 3, line 45, "is an and" should be --is an alkyl--.

Col. 5, line 29, "5one" should be --5-one--.

Col. 12, Comp. S-21 under N%, "1782." should be --17.82--.

Col. 12, Comp. S-25 under N%, "1693" should be --16.93--.

Col. 13, Comp. S-32 under melting point, "294-196" should be --294-296--.

Col. 17, Comp. S-61 under melting point, "223-14-225" should be --223-225--.

Signed and Sealed this

Twenty-seventh Day of August, 1991

Attest:

HARRY F. MANBECK, JR.

Attesting Officer

Commissioner of Patents and Trademarks